(12) United States Patent
Ferguson et al.

(10) Patent No.: US 9,782,161 B1
(45) Date of Patent: Oct. 10, 2017

(54) SUTURE LOCKING LOOPS AND METHOD OF USE

(71) Applicant: RIVERPOINT MEDICAL, LLC, Portland, OR (US)

(72) Inventors: Patrick Edward Ferguson, Portland, OR (US); Patrick Joseph Ferguson, Portland, OR (US); Wayne Jay Black, Portland, OR (US)

(73) Assignee: RIVERPOINT MEDICAL, LLC, Portland, OR (US)

( * ) Notice: Subject to any disclaimer, the term of this patent is extended or adjusted under 35 U.S.C. 154(b) by 123 days.

(21) Appl. No.: 14/669,323

(22) Filed: Mar. 26, 2015

(51) Int. Cl.
*A61B 17/04* (2006.01)
*A61B 17/06* (2006.01)

(52) U.S. Cl.
CPC ...... *A61B 17/04* (2013.01); *A61B 2017/0496* (2013.01)

(58) Field of Classification Search
CPC ............ A61B 17/0401; A61B 17/0469; A61B 17/0485; A61B 17/06166; A61B 2017/044; A61B 2017/0464; A61B 2017/0496; A61B 2017/0458; A61B 17/04; A61B 17/06; A61L 17/00
See application file for complete search history.

(56) References Cited

U.S. PATENT DOCUMENTS

| 7,601,165 | B2 * | 10/2009 | Stone | ................. | A61B 17/0401 606/232 |
| 2008/0082128 | A1 | 4/2008 | Stone | | |
| 2014/0276992 | A1 | 9/2014 | Stone et al. | | |

* cited by examiner

*Primary Examiner* — Victor Nguyen
(74) *Attorney, Agent, or Firm* — Timothy E. Siegel Patent Law, PLLC; Timothy E. Siegel

(57) ABSTRACT

A one-way loop locking suture assembly, that includes suture material, defining a lumen, with the suture material being comprised of a first terminal portion extending from the first end to a first broaching point, a medial portion extending from the first broaching to a second broaching point and a second terminal portion extending from the second broaching point to the second end. The first terminal portion enters into the lumen of the medial portion at the second broaching point, extends through the lumen of the medial portion and exits the lumen of the medial portion through the first broaching point, thereby forming a loop, wherein the medial portion includes the first terminal portion extending through the lumen of the medial portion. Accordingly, when the loop is tightened about a pair of pins, the lumen of the medial portion narrows, thereby retaining the first terminal length and preventing loosening.

6 Claims, 8 Drawing Sheets

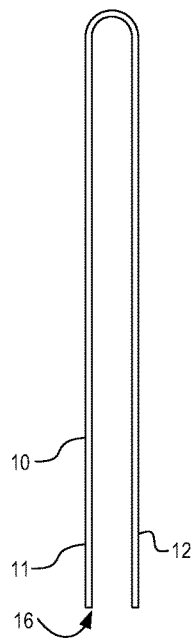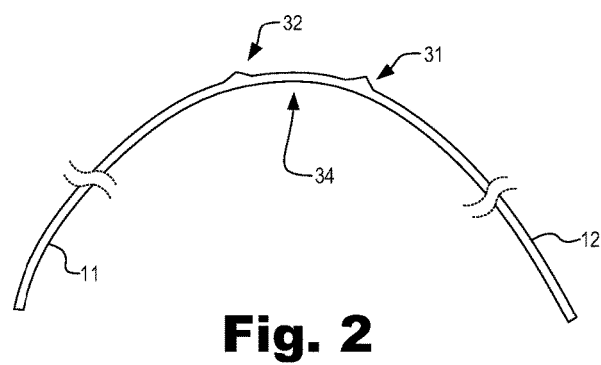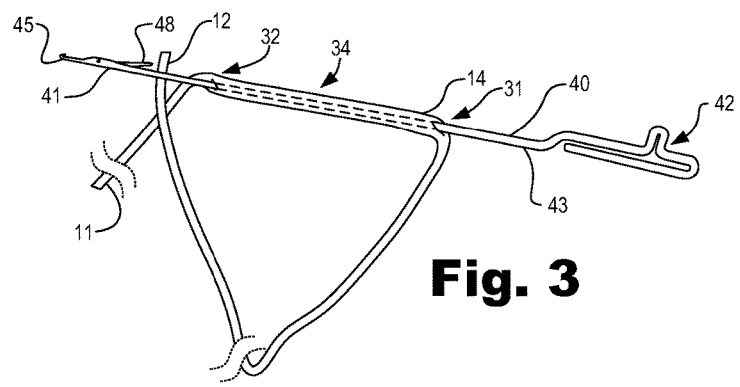
Fig. 1
Fig. 2
Fig. 3

SUTURE LOCKING LOOPS AND METHOD OF USE

FIELD

This invention relates to suture systems and more particularly, to soft suture anchors for use in orthopedic surgical techniques.

BACKGROUND

In veterinary practice the repair of a dog's stifle is a frequently performed type of surgery. To effect this repair, a pin is inserted into both of the two opposed bones of the stifle and a loop is drawn tight to keep these pins close together, thereby keeping the bones hinged together. U.S. Pat. No. 7,601,165 describes an apparatus that can be used for this purpose, but that is somewhat cumbersome and expensive. A simpler apparatus would ease the task faced by veterinarians. Also, various surgeries performed on human patients would benefit from a simpler apparatus for looping two pins together.

SUMMARY

The following embodiments and aspects thereof are described and illustrated in conjunction with systems, tools and methods which are meant to be exemplary and illustrative, not limiting in scope. In various embodiments, one or more of the above-described problems have been reduced or eliminated, while other embodiments are directed to other improvements.

In a first independent aspect, the invention may take the form of a one-way loop locking suture assembly, that includes suture material, defining a lumen, with the suture material being comprised of a first terminal portion extending from the first end to a first broaching point, a medial portion extending from the first broaching to a second broaching point and a second terminal portion extending from the second broaching point to the second end. The first terminal portion enters into the lumen of the medial portion at the second broaching point, extends through the lumen of the medial portion and exits the lumen of the medial portion through the first broaching point, thereby forming a loop, wherein the medial portion includes the first terminal portion extending through the lumen of the medial portion. Accordingly, when the loop is tightened about a pair of pins, the lumen of the medial portion narrows, thereby retaining the first terminal length and preventing loosening.

In a second independent aspect, the invention may take the form of a method of repairing a leg joint, including a femur and a tibia. The method utilizes a first bone screw and a second bone screw, and also a suture assembly that includes suture material, defining a lumen, with the suture material having a first end and an opposed second end, and being comprised of a first terminal portion extending from the first end to a first broaching point, a medial portion extending from the first broaching to a second broaching point and a second terminal portion extending from the second broaching point to the second end. Further, the first terminal portion enters into the lumen of the medial portion at the second broaching point, extends through the lumen of the medial portion and exits the lumen of the medial portion through the first broaching point. It thereby forms a suture loop, with the medial portion including the first terminal portion, which extends through the lumen of the medial portion. Returning to the steps of the method, the first bone screw is screwed into the femur and the second bone screw is screwed into the tibia. The suture loop is placed about the two screws and is cinched by pulling on the first and second end until the suture loop is cinched tight, thereby causing the lumen of the medial portion to narrow, thereby retaining the first terminal length and preventing loosening, so that the loop is locked in place. The locked loop couples the screws and thereby the femur and tibia together.

In a third independent aspect, the invention may take the form of a repaired non-human leg joint, including a femur and a tibia, and further including a first bone screw fastened into the femur and a second bone screw fastened into the tibia. Also, a suture assembly includes a suture loop that extends about the two screws and is cinched tight. This suture assembly has a structure that includes suture material, defining a lumen, and having a first end and an opposed second end, and including a first terminal portion extending from the first end to a first broaching point, a medial portion extending from the first broaching to a second broaching point and a second terminal portion extending from the second broaching point to the second end. The first terminal portion enters into the lumen of the medial portion at the second broaching point, extending through the lumen of the medial portion and exiting the lumen of the medial portion through the first broaching point, thereby forming the suture loop, such that the medial portion includes the first terminal portion extending through the lumen of the medial portion. Because the suture loop is cinched tight, the lumen of the medial portion is caused to narrow, thereby retaining the first terminal length and preventing loosening, so that the loop is locked in size, and thereby coupling the screws and thereby the femur and tibia together.

BRIEF DESCRIPTION OF THE DRAWINGS

FIG. 1 shows a side view of a suture in accordance with an embodiment.

FIG. 2 shows a side view of the suture of FIG. 1, at a further stage in the process.

FIG. 3 shows a side view of a suture construct in accordance with an embodiment, at a further stage in the process.

DETAILED DESCRIPTION OF THE PREFERRED EMBODIMENT

Figure 4:
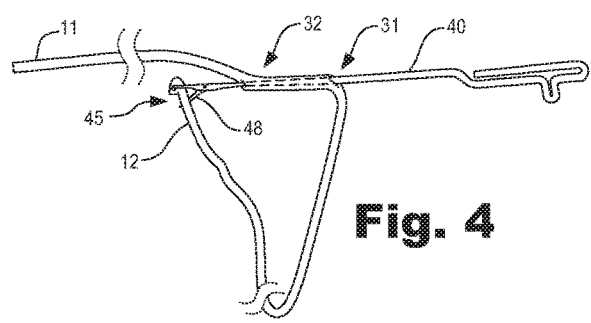
FIG. 4 shows a side view of a suture construct in accordance with an embodiment, at a yet further stage in the process.

References will now be made to embodiments illustrated in the drawings and specific language which will be used to describe the same. It will nevertheless be understood that no limitation of the scope of the invention is thereby intended, such alterations and further modifications in the illustrated devices, as such further applications of the principles of the invention as illustrated therein as being contemplated as would normally occur to one skilled in the art to which the invention relates.

Referring to FIGS. 1 and 2, there is shown a length of suture 10 having a suture first end 11 and a suture second end 12 opposite the suture first end 11. The suture 10 comprises a tubular braid structure defining a suture wall 13 (FIG. 9) having a suture outer surface 14 (FIG. 3) and a lumen 16 therethrough. In this embodiment, the suture second end 12 is inserted into the lumen 16 through an aperture in the suture wall 13 so as to extend for a predetermined distance within the lumen 16, and exits the lumen 16 though another aperture in the suture wall 13. A first penetration point 31 and a second penetration point 32 a predetermined distance from the first penetration point 31 are defined. The first penetration point 31 and second penetration point 32 are located a predetermined distance from the suture first end 11 and suture second end 12 and define a passageway portion 34 therebetween, as shown in FIG. 2.

A lacing tool 40 (FIG. 3) is used in a further set of operations. Tool 40 has an elongated shaft 43, which has a shaft first end 41 and a shaft second end 42, and a handle (not shown) optionally formed in the shaft second end 42. Further, the shaft first end 41 is formed into a hook 45, and also includes a lever 48 pivotally coupled to the shaft first end 41, adjacent the hook 45 but operable to close the hook 45 in a first position and to open the hook 45 in a second position, as shown in FIG. 3. The hook 45 of the lacing tool 40 is advanced from the suture outer surface 14 to the lumen 16 at the first penetration point 31 by advancing the hook 45 through the strands of the braid without breaking the strands. Then, the hook 45 is advanced to the second penetration point 32 within the lumen 16. Finally, the hook 45 is advanced from the lumen 16 to the suture outer surface 14 at the second penetration point 32 by advancing the hook 45 through the strands of the braid without breaking the strands, with a portion of the shaft 43 extending through the lumen 16 between the first penetration point 31 and the second penetration point 32, as shown in FIG. 3.

Figure 5:
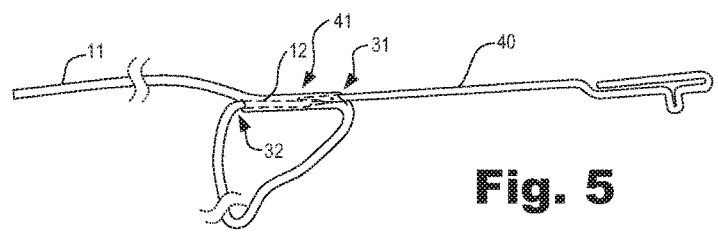
FIG. 5 shows a side view of a suture construct in accordance with an embodiment at a still further stage in the process.
Figure 6:
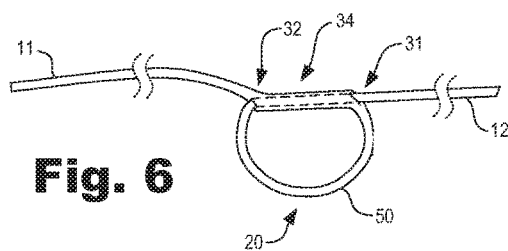
FIG. 6 shows a side view of a suture locking loop, in accordance with an embodiment.

Then, the suture second end 12 is placed into the hook 45 and the lever 48 is closed, to affirmatively retain end 12 in hook 45, as shown in FIG. 4. As shown in FIG. 5, the hook 45 is then pulled, so as to pull the suture second end 12 through the second penetration point 32, into and through the lumen 16 and out of the first penetration point 31, thereby forming a loop 50. Referring to FIG. 6, the lacing tool 40 (FIG. 6) is then removed from the suture 10, leaving the loop 50, which acts as a locking loop, not loosening while being forcefully pulled, in what is now finished assembly 20.

Figure 7:
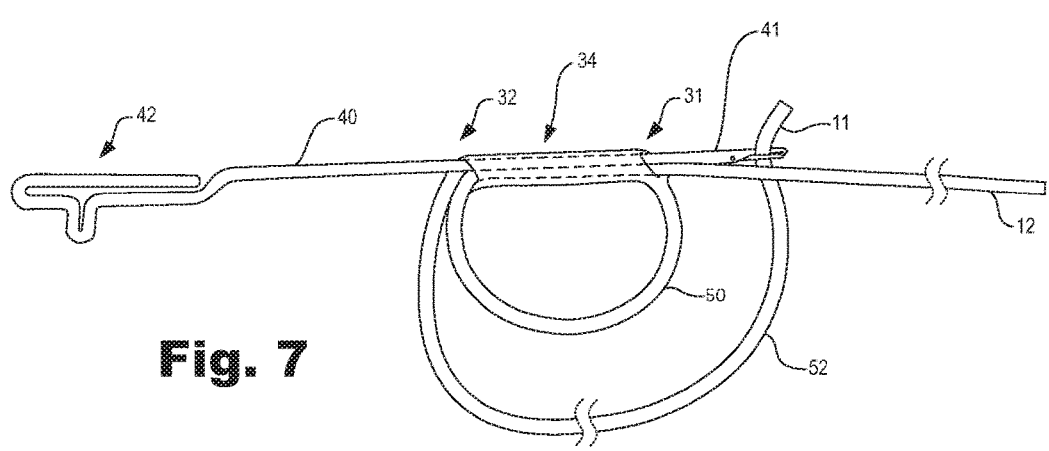
FIG. 7 shows a side view of a suture construct that represents an intermediate step in the production of a double locking loop, from the locking loop of FIG. 6.
Figure 8:
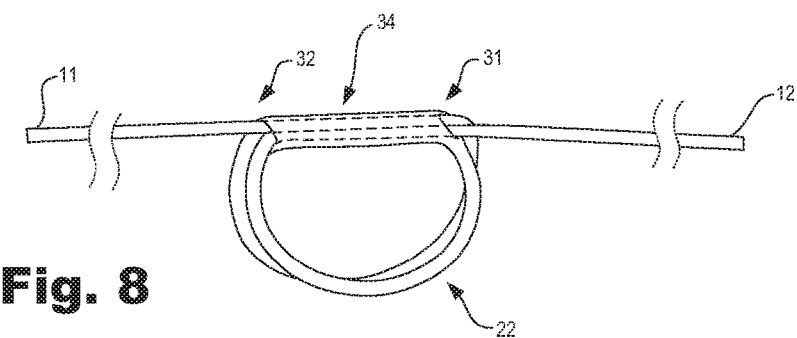
FIG. 8 shows a side view of a double locking loop in accordance with an embodiment.
Figure 9:
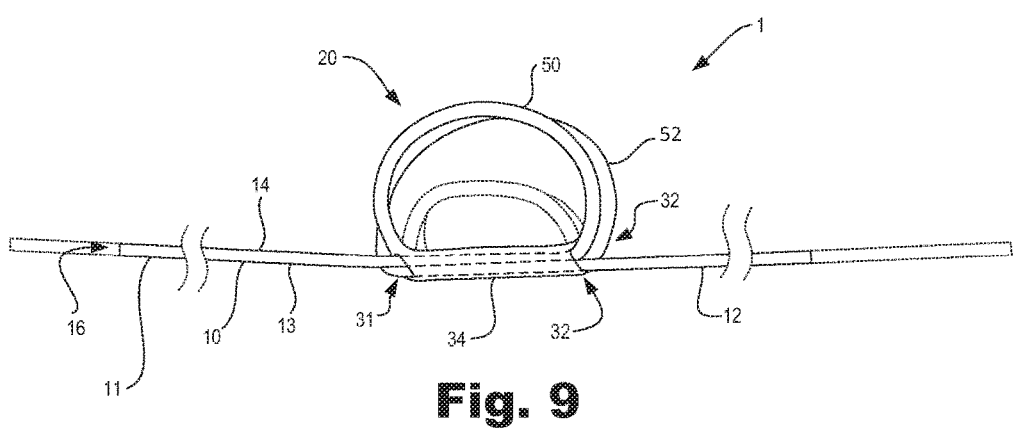
FIG. 9 shows a side view of the double locking loop of FIG. 8, as the loops are being cinched.

The suture assembly shown in FIG. 6 may be used as a finished product, or may be used as a workpiece for the construction of a further embodiment, in a method shown in FIGS. 7 and 8. Referring to FIG. 6, the hook 45 of the lacing tool 40 is advanced through the suture outer surface 14 to the lumen 16 at the second penetration point 32 by advancing the hook 45 through the strands of the braid without breaking the strands. Then, the hook 45 is advanced to the first penetration point 31 within the lumen 16. The hook 45 is then advanced from the lumen 16 to the suture outer surface 14 at the first penetration point 31, with a portion of the shaft 43 (FIG. 3) extending through the lumen 16 between the second penetration point 32 and the first penetration point 31. Then, the suture first end 11 is placed into the hook 45 and the lever 48 is closed, as shown in FIG. 7. The hook 45 is pulled so as to pull the suture first end 11 into the first penetration point 31, through the lumen 16 and out of the second penetration point 32 forming a second loop 52 and removing the lacing tool 40 from the suture 10, wherein the first loop 50, the second loop 52 and the passageway portion 34 define a double locking loop suture assembly 22, as shown in FIG. 8. FIG. 9 shows the assembly of FIG. 8, with the loops being constricted.

Figure 10:
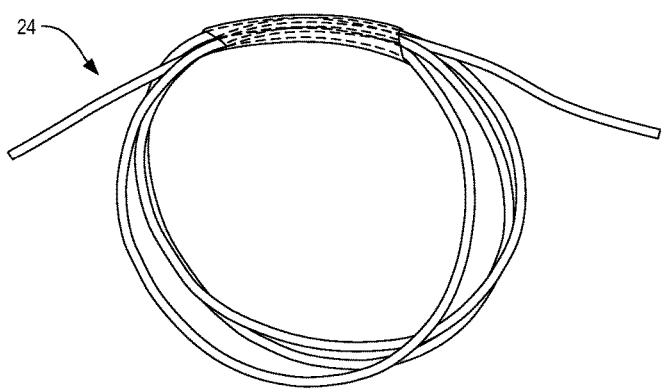
FIG. 10 shows a side view of a triple locking loop in accordance with an embodiment.
Figure 11:
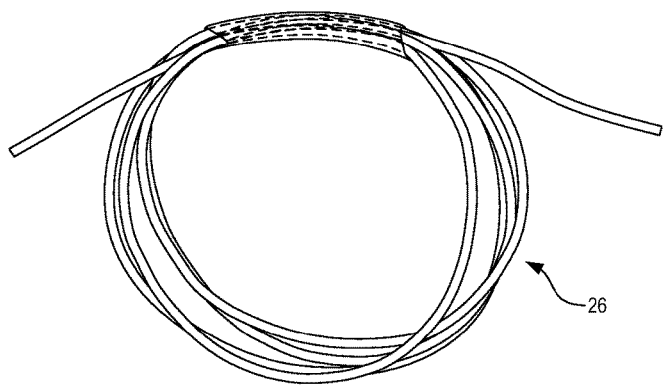
FIG. 11 shows a side view of a quadruple locking loop in accordance with an embodiment.

It is appreciated that the method of forming the first loop 50 and second loop 52 may be repeated so as to form any number of loops, such as loop 50, suitable for a particular purpose. Limiting factors for the number of first loops may be the size of the lumen or the size of the penetration holes at the first penetration point 31 and the second penetration point 32. FIG. 10 shows an embodiment having three locking loops, whereas FIG. 11 shows an embodiment having four locking loops.

Figure 12:
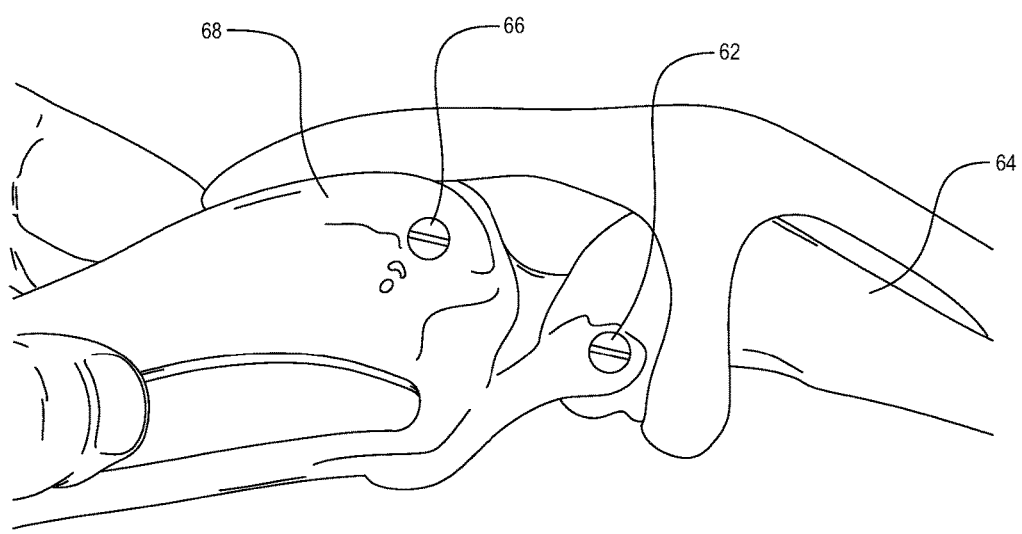
FIG. 12 shows a side view of dog stifle, into which a pin has been introduced into each one of two opposing bones.
Figure 13:
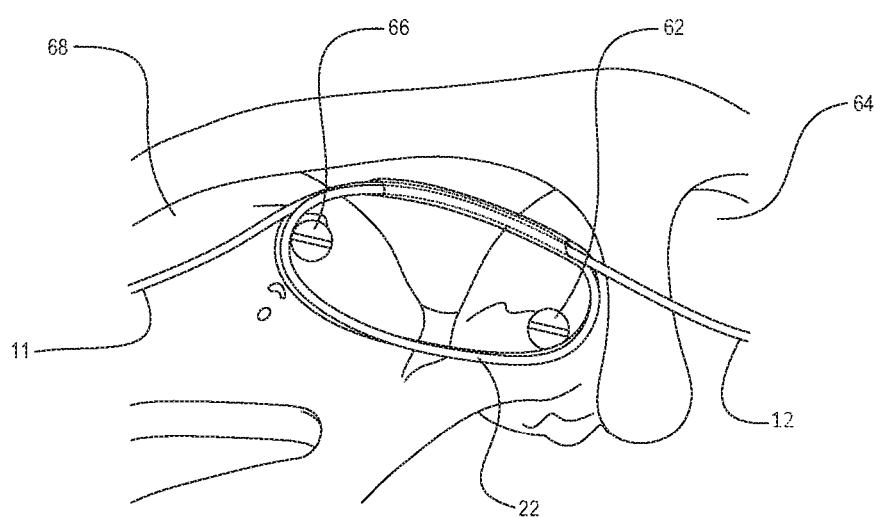
FIG. 13 shows the dog stifle and pins of FIG. 12, with a double locking loop, introduced over the pins.
Figure 14:
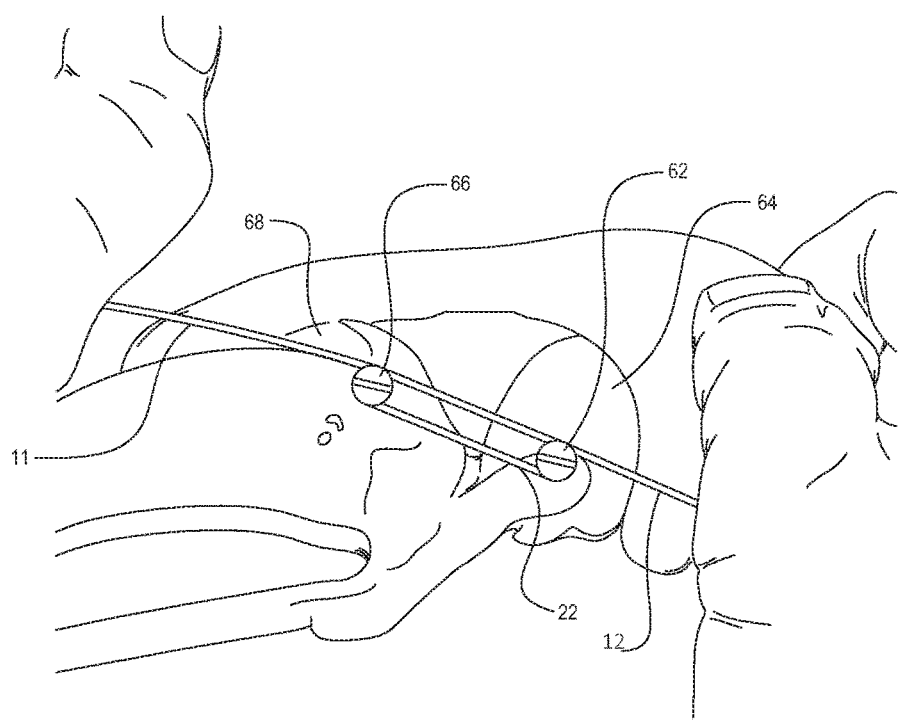
FIG. 14 shows the dog stifle, pins and double locking loop of FIG. 13.

Referring to FIGS. 12 through 14, a method of repairing a leg joint, according to the present invention, starts with a first bone screw 62 being introduced into the femur 64, and a second bone screw 66 is introduced into the tibia 68 (FIG. 12). In one preferred embodiment, the leg joint is more specifically a dog stifle wherein the cranial cruciate ligament has been damaged. Bone screws, such as screws 62 and 66, typically have a head and a threaded shank (not shown), and can be introduced into bone by pressing downwardly on the head, while the screw is rotated, thereby driving the threaded shaft into the bone. A double locking loop 22 (FIG. 13) is introduced about the bone screws 62 and 66 and cinched tight by ends 11 and 12 (FIG. 14). Ends 11 and 12 may then be cut back and the incision sewn together. In additional embodiments, the single locking loop 20 of FIG. 6, or a triple locking loop 24 of FIG. 10 or quadruple locking loop 26 of FIG. 11, may be used.

In a preferred embodiment, suture length 10, and therefore locking loop assemblies 20, 22, 24 and 26 are made of ultra high molecular weight polyethylene.

While the invention has been described in connection with specific embodiments thereof, it will be understood that it is capable of further modification, and this application is intended to cover any variations, uses, or adaptations of the invention following, in general, the principles of the invention and including such departures from the present disclosure as come within known or customary practice in the art to which the invention pertains and as may be applied to the essential features hereinbefore set forth, and as fall within the scope of the invention and the limits of the appended claims.

We claim:

1. A method of repairing a leg joint, including a femur and a tibia, and comprising:
   (a) providing a first bone screw and a second bone screw;
   (b) providing a suture assembly including:
      (i) suture material, defining a lumen, said suture material having a first end and an opposed second end, and being comprised of a first terminal portion extending from said first end to a first broaching point, a medial portion extending from said first broaching to a second broaching point and a second terminal portion extending from said second broaching point to said second end; and (ii) said first terminal portion entering into said lumen of said medial portion at said second broaching point, extending through said lumen of said medial portion and exiting said lumen of said medial portion through said first broaching point, thereby forming a suture loop, wherein said medial portion includes said first terminal portion extending through said lumen of said medial portion;

(c) screwing said first bone screw into said femur;

(d) screwing said second bone screw into said tibia; and (e) placing said suture loop about said two screws and pulling said first and second ends until said suture loop is cinched tight, thereby causing said lumen of said medial portion to narrow, thereby retaining said first terminal length and preventing loosening, so that said loop is locked in size, and coupling said screws and thereby said femur and tibia together.

2. The method of claim 1, further wherein said second terminal portion enters into said lumen of said medial portion at said first broaching point and extends through said lumen of said medial portion and exits said lumen of said medial portion through said second broaching point, thereby forming a second loop, and wherein both loops are placed about said two screws.

3. The method of claim 2, further wherein said first terminal portion re enters into said lumen of said medial portion at said second broaching point, extends through said lumen of said medial portion, a second time, and exits said lumen of said medial portion through said first broaching point, a second time, thereby forming a third loop, and wherein all three are placed about said two screws.

4. The method of claim 3, further wherein said second terminal portion re enters into said lumen of said medial portion at said first broaching point and re-extends through said lumen of said medial portion and re exits said lumen of said medial portion through said second broaching point, thereby forming a fourth loop, and wherein all four loops are placed about said two screws.

5. The method of claim 1, wherein said leg joint is more specifically a dog stifle.

6. The method of claim 1, wherein the cranial cruciate ligament has been damaged.

* * * * *